United States Patent [19]

Heaton et al.

[11] Patent Number: 5,981,791

[45] Date of Patent: Nov. 9, 1999

[54] HIGH PURITY N-(4-[N,N-BIS(2-IODOETHYL)AMINO]PHENOSCYCARBONYL)-L-GLUTAMIC ACID

[75] Inventors: David William Heaton; Susan Dines; Robert Ian Dowell, all of Macclesfield, United Kingdom

[73] Assignee: Zeneca Limited, London, United Kingdom

[21] Appl. No.: 08/860,880

[22] PCT Filed: Dec. 21, 1995

[86] PCT No.: PCT/GB95/02997

§ 371 Date: Jun. 23, 1997

§ 102(e) Date: Jun. 23, 1997

[87] PCT Pub. No.: WO96/20169

PCT Pub. Date: Jul. 4, 1996

[30] Foreign Application Priority Data

Dec. 23, 1994 [GB] United Kingdom .................. 9426133

[51] Int. Cl.⁶ .................................................. C07C 261/00
[52] U.S. Cl. ......................... 560/136; 560/160; 560/163; 514/548

[58] Field of Search ............................... 560/136; 514/548

[56] References Cited

U.S. PATENT DOCUMENTS 5,405,990  4/1995  Burke et al. .
5,587,161  12/1996  Burke et al. .
5,660,829  8/1997  Burke et al. .

FOREIGN PATENT DOCUMENTS 94 02450  3/1994  WIPO .

*Primary Examiner*—Paul J. Killos
*Attorney, Agent, or Firm*—Pillsbury Madison & Sutro Intellectual Property Group

[57] ABSTRACT

A new salt of a prodrug useful in antibody directed enzyme prodrug therapy (ADEPT) is disclosed. A hydrogen iodide salt of the prodrug N-(4-[N,N-bis(2-iodoethyl)amino] phenoxycarbonyl)-L-glutamic acid is prepared which can be obtained in crystalline form. Preparation of the crystalline form of the prodrug enables preparation of the prodrug in highly pure form.

16 Claims, 4 Drawing Sheets

Formula 1

HIGH PURITY N-(4-[N,N-BIS(2-IODOETHYL) AMINO]PHENOSCYCARBONYL)-L-GLUTAMIC ACID

This application is the national phase of international application PCT/GB95/02997, filed Dec. 21, 1995 which was designated the U.S.

The present invention relates to a known prodrug useful in Antibody Directed Enzyme Prodrug Therapy (ADEPT) in a new highly purified form and a new salt of the prodrug, pharmaceutical compositions thereof and processes for making the salt.

The prodrug N-(4-[N,N-bis(2-iodoethyl)amino] phenoxycarbonyl)-L-glutamic acid was disclosed on Feb. 3, 1994 in international patent application WO 94/02450; see Example 33 therein which describes a trifluoroacetic acid (TFA) salt which is produced as a gum. The known gum form of the prodrug was not able to be very highly purified because of the known difficulties of handling gum type compounds. There has been no disclosure whatsoever of a hydrogen iodide salt of the prodrug or of the prodrug per se in highly pure form.

According to one aspect of the present invention there is provided N-(4-[N,N-bis(2-iodoethyl)amino] phenoxycarbonyl)-L-glutamic acid in substantially pure form.

The term "in substantially pure form" means that the prodrug is at least 95% pure (preferably at least 96% pure, more preferably at least 97% pure, more preferably at least 98% pure) in relation to reaction contaminants, including solvents, carried over from any synthesis of the prodrug. These high levels of purity have only become possible by the invention disclosed herein of the hydrogen iodide salt of the prodrug which can be produced in crystalline form. The crystalline form of the prodrug allows the prodrug to be easily obtained in a highly purified state because the salt can be efficiently collected from the reaction mixture and washed with solvent to remove contaminants, including solvents, from the synthetic procedure. Preferably the substantially pure prodrug is in a dry form mixed with a buffer suitable for intravenous administration after reconstitution.

According to another aspect of the present invention there is provided a hydrogen iodide salt of N-(4-[N,N-bis (2-iodoethyl)amino]phenoxycarbonyl)-L-glutamic acid. Preferably the salt is in substantially pure form. Preferably the hydrogen iodide salt of N-(4-[N,N-bis(2-iodoethyl) amino]phenoxycarbonyl)-L-glutamic acid is in crystalline form. Preferably the crystalline form has a melting point of 142–145° C. Preferably the crystalline form has an X-ray powder diffraction spectrum substantially as shown in FIG. 3.

The salt has the following advantages: good thermal stability; easier synthesis and purification because it can be collected efficiently from the reaction mixture; increased purity and reduced hygroscopic/deliquescence properties which further facilitate handling.

Whilst not wishing to be bound by theoretical considerations it is believed that the presence of HI somehow helps to reverse any degradation of the prodrug in the region of the mustard alkylating arms. It is believed that products derived from an aziridene intermediate may be produced on storage or heat stress when the prodrug is stored in the dry state. The HI salt of the prodrug is advantageously stable when dissolved in aqueous solution possibly due to in situ generation of iodide counter ion. A person skilled in the art would not be likely to add the likes of high concentration NaI to this prodrug for its pharmaceutical use (the only known use) because of pharmaceutical effects per se in such compounds.

According to another aspect of the present invention there is provided a pharmaceutical composition comprising N-(4-[N,N-bis(2-iodoethyl)amino]phenoxycarbonyl)-L-glutamic acid in substantially pure form and a pharmaceutically acceptable excipient.

Preferably the composition is supplied as a dry form. Preferably the excipient is a buffer, especially sodium bicarbonate. Preferably the composition is reconstituted shortly before use as an ADEPT component preferably with a sterile diluent.

According to another aspect of the present invention there is provided a two component pharmaceutical composition comprising a first component of hydrogen iodide salt of N-(4-[N,N-bis(2-iodoethyl)amino]phenoxycarbonyl)-L-glutamic acid in dry form and a second component of sterile diluent. Preferably the salt is in crystalline form.

According to another aspect of the present invention there is provided a process of making a hydrogen iodide salt of N-(4-[N,N-bis(2-iodoethyl)amino]phenoxycarbonyl)-L-glutamic acid in which the process comprises deprotecting a compound of Formula 1 (see FIG. 4) wherein Pr1 and Pr2 represent protecting groups (preferably Pr1 and Pr2 are tertiarybutyl ester groups or trimethylsilyl groups, especially trimethylsilyl). Deprotection is preferably performed under acid conditions in an inert atmosphere in the presence of HI to produce a hydrogen iodide salt of N-(4-[N,N-bis(2-iodoethyl)amino]phenoxycarbonyl)-L-glutamic acid. Preferably the deprotection is performed in the presence of an aprotic solvent, preferably dichloromethane or toluene, especially dichloromethane. Preferably the deprotection takes place in 2 stages wherein Pr1 and Pr2 are replaced by different protecting groups Pr3 and Pr4 but 1-stage deprotection by HI is also contemplated. Preferably for 2-stage deprotection the compound of formula 1 is treated with iodotrimethylsilane (TMSI). Pr3 and Pr4 are preferably trimethylsilyl (TMS) protecting groups which are then preferably removed under acid conditions, preferably containing seed. For 2-stage deprotection the first step is generally 30 min–24 h, especially 4–6 h and the second step is generally 1–48 h, preferably 12–18 h at ambient temperature (15–30° C.). Extended stirring, preferably for at least about 14 h (especially at least about 18 h), preferably at ambient temperature, is important for crystallisation.

DESCRIPTION OF DRAWINGS

The invention is illustrated below in the following non-limiting examples in which.

EXAMPLE 1

Figure 1:
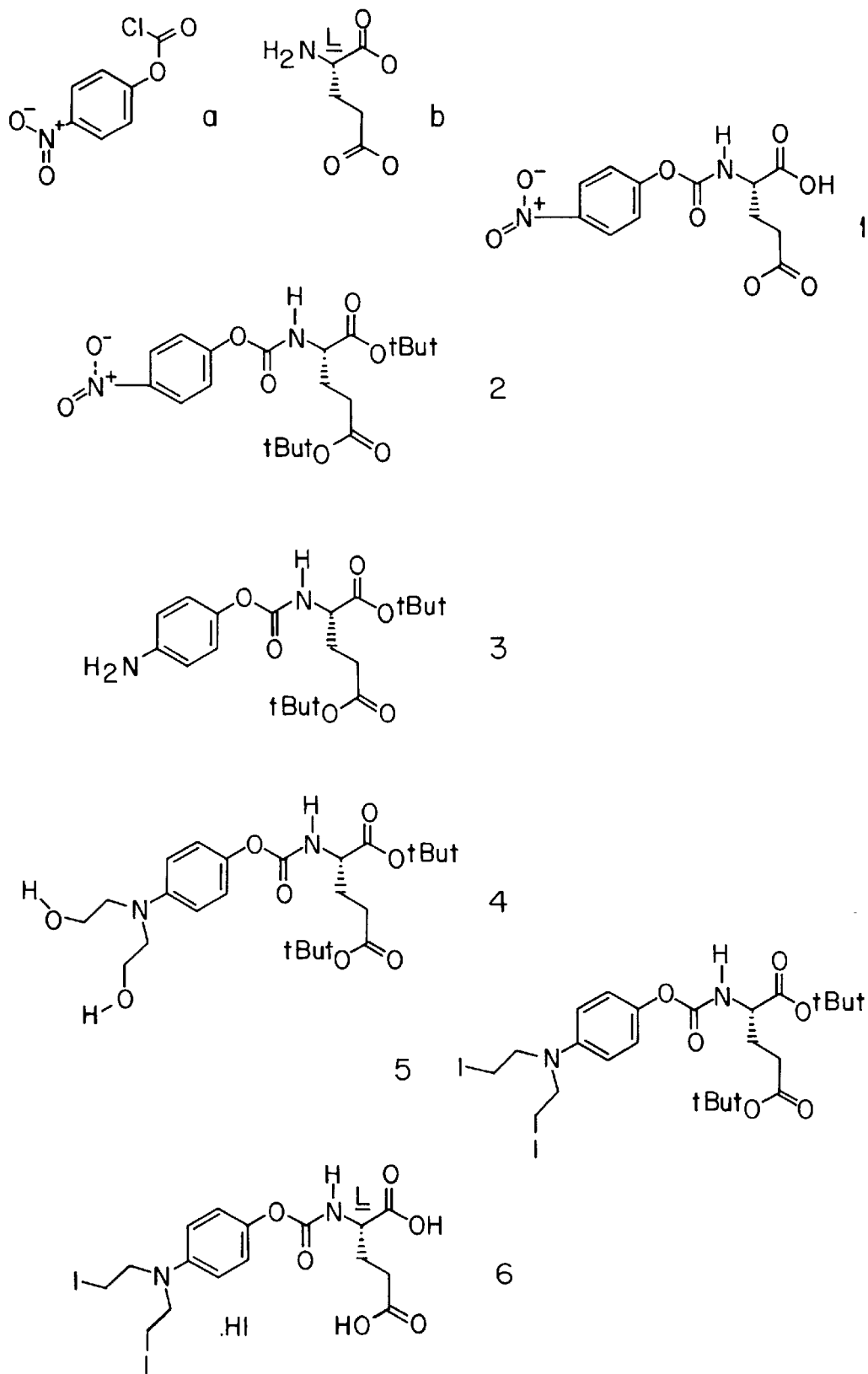
FIG. 1 shows chemical Formulae.
Figure 2:
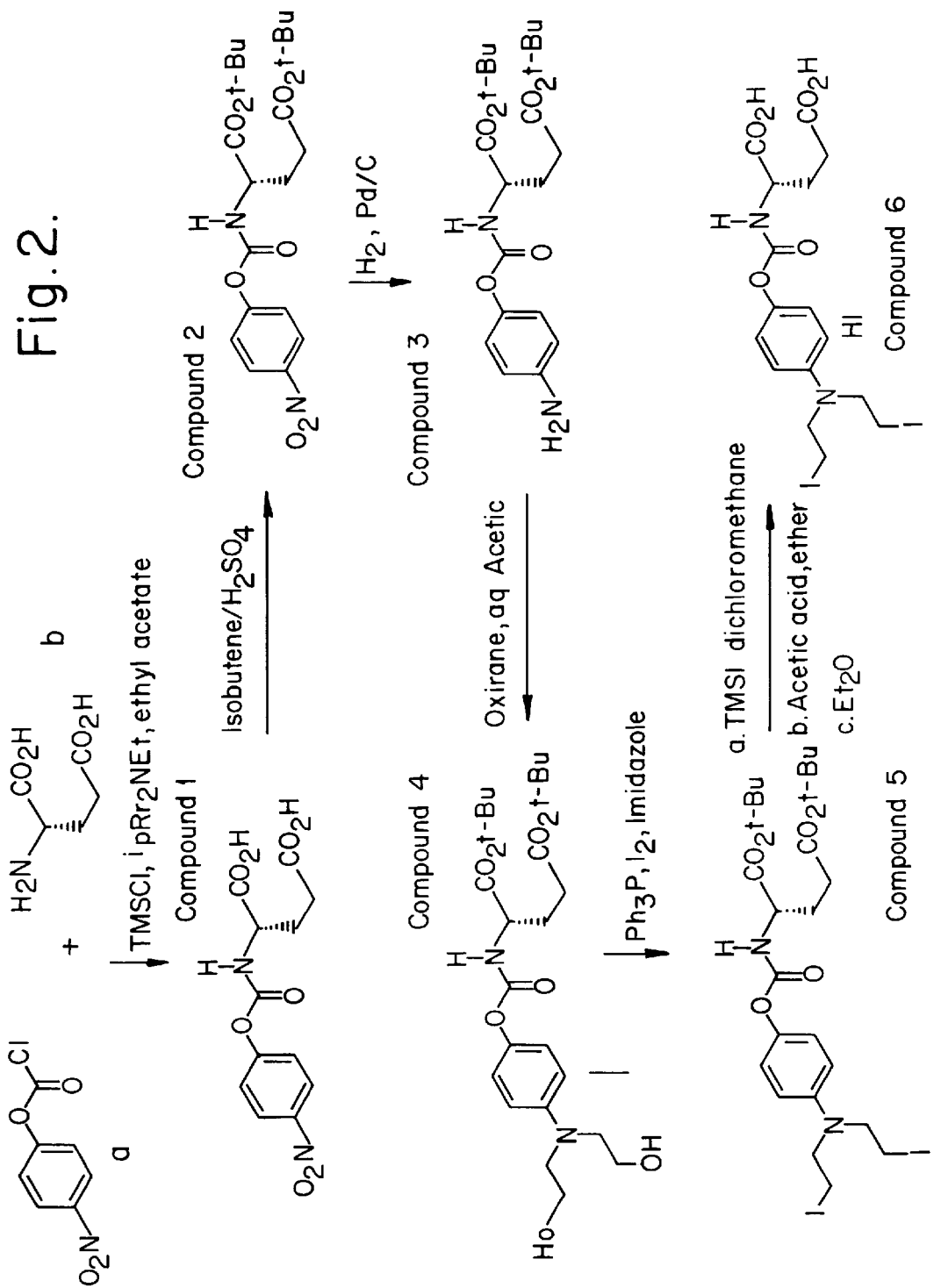
FIG. 2 shows a synthetic route to the HI salt of the prodrug N-(4-[N,N-bis(2-iodoethyl)amino] phenoxycarbonyl)-L-glutamic acid.

Preparation of Hydrogen Iodide Salt of N-(4-[N,N-bis(2-iodoethyl)amino]phenoxy-carbonyl)-L-glutamic Acid (See FIGS. 1 & 2)

N-(4-[N,N-bis(2-iodoethyl)amino]-phenoxycarbonyl)-L-glutamic acid di-tertiarybutyl ester (FIG. 1, compound 5; 25.9 g) was dissolved in dichloromethane (173 ml) under nitrogen at ambient temperature. To this solution was added iodotrimethylsilane (26.2 ml) and the reaction agitated for 4–6 hours. Once reaction is complete the solution was slowly drowned out into a mixture of diethyl ether (834 ml) and acetic acid (43 ml) preferably containing seed crystals of end product (first time through the reaction still works). The resulting suspension was left to stir for 18 hours at ambient temperature to obtain a crystalline form. Note this prolonged stirring is important to achieve crystallisation. The desired end product, the hydrogen iodide salt of N-(4-[N,N-bis(2-iodoethyl)amino]phenoxycarbonyl)-L-glutamic acid (FIG. 1, compound 6), in crystalline form was filtered off, washed with diethyl ether (2×150 ml), and dried to constant weight in a vacuum oven. Weight of product=22.1 g.

M.P.=142–5° C. (decomp) Optical Rotation:—$[\alpha]D^{25}$=–21.1° (C=1, Dimethylformamide) NMR (DMSOd$_6$): $\delta$7.93 (d, 1H); 6.91 (d, 2H); 6.63 (d, 2H); 4.0 (m, 1H); 3.69 (t, 4H); 3.28 (t, 4H); 2.33 (m, 2H); 2.0 (m, 1H); 1.8 (m, 1H). $^{13}$C Chemical Shifts (relative to DMSO at 39.6$\delta$):—3.9, 52.9, 143.0, 112.1, 122.6, 142.0, 154.9, 53.2, 26.1, 30.1, 173.6, 173.2 Elemental Analysis:—$C_{16}H_{20}I_2N_2O_6$.HI. Found C 26.9%, H 3.1%, N 3.8%, I 52.7% Theory: C 26.7%, H 3.0%, N 3.9%, I 52.9%

N-(4-[N,N-bis(2-iodoethyl)amino)-phenoxycarbonyl)-L-glutamic acid di-tertiarybutyl ester (FIG. 1, compound 5) was prepared as set out below.

a) Preparation of N-(4-nitro-phenoxycarbonyl)-L-glutamic acid (compound 1 in FIG. 1)

L-Glutamic acid (FIG. 1, compound b; 73.6 g) was suspended in dichloromethane (750 ml) under an atmosphere of nitrogen in a 2 L flask. N,N-Diisopropylethylamine (193.9 g) was added in one portion, chlorotrimethyl silane (135.8 g) added over 20 minutes whilst maintaining the reaction mixture at or below reflux (see Note 1). After complete addition the reaction mixture was refluxed for 1.5 hours then cooled to 1° C. to give L-glutamic acid bis-trimethylsilyl(TMS) ester.

In a clean, dry 3 L reactor under an atmosphere of nitrogen, p-nitrophenyl chloroformate (FIG. 1, compound a; 100.8 g) was dissolved in dichloromethane (375 ml) and the solution was cooled to –3° C. The previously formed solution of L-glutamic acid bis-TMS ester was then added over 15 minutes maintaining the temperature below 10° C. After complete addition, the mixture was stirred for 15 minutes then cooled to about 5° C. A solution of dilute HCl was prepared from water (750 ml) and conc. HCl (148 ml). The dichloromethane solution was then added over 15 minutes, maintaining the temperature at about 20° C. After complete addition, the mixture was stirred at 20° C. for 30 minutes then allowed to settle for 30 minutes; this gave three layers. The bottom layer was run off and discarded and product was extracted twice with methyl isobutyl ketone (MIBK; 1000 ml, 500 ml). The two organic layers were combined, washed with saturated NaCl (250 ml) and solvent removed under reduced pressure (bath temp. 40° C.) to give a white solid. The product was dissolved in ethyl acetate (600 ml) at 40° C. then hexane (600 ml) was added, the mixture cooled to 20° C. with stirring, stirred overnight then isolated by filtration. The desired product 126 g (77% yield) was washed with 1:1 ethyl acetate/hexane (300 ml), then dried at 50° C. to constant strength.

Note 1

Addition of the chlorotrimethylsilane causes the temperature to rise from 13° C. to 40° C. if no cooling is applied.
Characterisation of Compound NMR (DMSOd$_6$) $\delta$ 8.45 (d, 1H); 8.25 (d, 2H); 7.4 (d, 2H); 4.07 (m, 1H); 2.35 (m, 2H); 2.05 (m, 1H); 1.85 (m, 1H).

b) Preparation of N-(4-nitro-phenoxycarbonyl)-L-glutamic acid di-tertiarybutyl ester (Compound 2 in FIG. 1)

The product from step a) (FIG. 1, compound 1; 2120 g) was charged to a 100 L reactor and methyl isobutyl ketone (24 liters) added. The resulting slurry was heated to 50° C. to effect dissolution and afterwards the solution was cooled to 0–5° C. and concentrated sulphuric acid (700 ml) added over 10 minutes at 0–5° C.

Isobutylene was condensed into a 10 liter premarked empty vessel at –25° C. to –30° C. and using a stream of Argon, isobutylene was transferred to the reaction mixture over 18 minutes at 0–5° C. The mixture was warmed to 18–20° C. over 2 hours and then left to stir for 18 hours at 18–20 ° C.

Sodium bicarbonate solution (2332 g in 27.1 liters of water) was cooled to 0–5° C. using an ice water bath and the reaction mixture added to it over 20 minutes. The mixture was stirred and warmed to 18–20° C. and then left to stand to achieve separation of the two layers. The organic phase (upper layer) was separated and washed with 9.87 liters of 0.36 M potassium dihydrogen orthophosphate buffer (which is prepared by dissolving 530 g of potassium dihydrogen orthophosphate in 9.87 liters of water).

The organic phase is separated and then reduced on the rotary evaporator to leave an amber coloured oil (2334 g) containing the required product.

NMR (DMSOd$_6$): $\delta$ 7.33 (d, 2H); 8.24 (d, 2H); 5.90 (d, 1H); 4.32 (m, 1H); 2.0–2.4 (m, 4H); 1.50 (s, 9H); 1.46 (s, 9H).

c) Preparation of N-(4-amino-phenoxycarbonyl)-L-glutaric acid di-tertiarybutyl ester (Compound 3 in FIG. 1)

To a suitably serviced hydrogenation vessel was charged 10% palladium on carbon (200 g of water wet paste), followed by a solution of Compound 2 (1.0 kg) in n-butyl acetate (5 L). The agitated suspension was cooled to 15° C. then hydrogenated using a slight positive pressure (0.1 bar) of hydrogen, maintaining the temperature at 15–25° C. with external cooling (note 1). When hydrogen uptake ceased the catalyst was filtered off and washed with n-butyl acetate (2×500 ml). The combined filtrates were washed with a solution of 100 Tw sodium hydroxide (0.114 L; specific gravity 1.5 g/ml, 46–48% w/v) made up to 2 L with water, then water (2×2 L). The organic layer (approximately 7 L) was evaporated under reduced pressure at 35–45° C. until the volume was approximately 2l. The agitated solution was heated to 50–55° C., then Essochem Solvent 30™ (5 L; a hydrocarbon solvent available from Exxon Chemical Ltd, PO Box 122, 4600 Parkway, Fareham, Hampshire PO15 7AP, UK; note an alternative solvent such as hexane could be used) added whilst maintaining the temperature at 50–55° C. The mixture was cooled to +5° C. and filtered. The isolated solid was washed twice with a mixture of n-butyl acetate (250 ml) and Essochem Solvent 30™ (750 ml), pulled dry and dried at room temperature under vacuum to give 0.54 kg of the desired product.

Note 1

The hydrogenation is exothermic.

NMR of product (DMSOd$_6$) $\delta$: 7.80 (d,1H), 6.45–6.75 (m,4H), 4.95 (bs, 2H), 3.95 (m, 1H), 2.4 (m,2H), 1.7–2.0 (m,2H), 1.4 (18H). FAB MS [MH+] 395 d) Preparation of N-(4-[N,N-bis(2-hydroxyethyl)amino]-phenoxycarbonyl)-L-glutamic acid di-tertiarybutyl ester (Compound 4 in FIG. 1)

The product from step c) (Compound 3, 60 g) was dissolved in acetic acid (430 ml) and water (430 ml) added to give a cloudy solution. The agitated solution was treated with ethylene oxide gas (78 g), over several hours whilst maintaining the temperature below 30° C. A solid CO$_2$ condenser was used to trap any excess gas. The mixture was allowed to stir for at least 18 hours then sampled for an end of reaction check by thin layer chromatography. The mixture was then evaporated to dryness under reduced pressure using a "cold finger" Buchi Rotovapor. The resulting oil was dissolved in ethyl acetate (600 ml), washed with a solution of sodium hydrogen carbonate (25 g) in water (350 ml). The separated organic layer was washed twice with water (250 ml), dried over magnesium sulfate, filtered, then evaporated under reduced pressure to an oil (77 g) containing the required product (50% strength approximately).

The required product was crystallised as follows. The product (57 g @ 82% strength) was dissolved at 40° C. in ethyl acetate (228 ml) then cooled to 22° C. and carbon Darko KB (5.7 g; available from Norit UK Ltd, Clydesmill Place, Cambuslang Industrial-Estate, Glasgow G32 8 RF) added. The mixture was stirred for 90 minutes, then filtered through celite, washing the cake with ethyl acetate (57 ml). The resulting solution was heated to 50° C. and hexane fraction (570 ml) added at 45–50° C. over 45 minutes. Once addition was complete the solution was allowed to self cool, seeding at 35° C. then stirring overnight. The mixture was chilled to 15° C. for 1 hour then filtered and washed with 2:1 hexane fraction/ethyl acetate (45 ml) then hexane fraction (45 ml) before drying at 50° C.

Weight of product=35.7 g (76% yield). Melting point= 91–93° C. NMR (DMSOd$_6$) δ: 6.85 (d, 2H); 6.6 (d, 2H); 4.65 (m, 1H).

e) Preparation of N-(4-[N,N-bis(2-iodoethyl)amino]-phenoxycarbonyl)-L-glutamic acid di-tertiarybutyl ester (Compound 5 in FIG. 1)

Triphenylphosphine (32.6 g) was dissolved in dichloromethane (200 ml) under nitrogen, imidazole (8.4 g) added and when complete solution is obtained the solution is chilled to 5° C. Iodine (31.5 g) was added in portions whilst keeping the temperature below 21° C. When the addition was complete the reaction mixture was allowed to warm to room temperature over 1 hour. A solution of product from step d) (20.0 g) in dichloromethane (50 ml) was added whilst keeping the temperature below 26° C. and the reaction mixture left to sir overnight until reaction was complete. After cooling to 5° C. 10% potassium iodide solution (120 ml) was added whilst keeping the temperature below 10° C. After settling for approx 10 minutes the lower organic layer was separated off. The solvent was removed by evaporation and the oily residue dissolved in ethyl acetate (100 ml). Cyclohexane (200 ml) was added to the mixture slowly to precipitate the triphenylphosphine oxide and after stirring for at least 10 minutes the solid was filtered off and washed with (2:1) cyclohexane/ethyl acetate (60 ml). The filtrate was evaporated and the residue triturated in tert-butylmethyl ether (MTBE) (200 ml). This suspension was filtered through a silica column (100 g) washing with MTBE (2×100 ml). The combined organics were evaporated to give the desired product as a colourless oil (26.0 g). NMR (CDCl$_3$) δ 7.0 (d, 2H); 6.6 (d, 2H); 5.4 (d, 1H); 4.3 (m, 1H); 3.7 (t, 4H); 3.2 (t, 4H); 2.4–1.9 (m, 4H); 1.5 (s, 9H); 1.45 (s, 9H).

EXAMPLE 2

Pharmaceutical Composition

3×20 ml type 1 glass vials each containing 610 mg of prodrug and three ampoules, each containing 11 ml of 2.15% w/v sodium hydrogen carbonate, for final dosage form preparation. Needles (3×18 G) and hydrophobic filters for venting the vials and 3× single use sterile 0.22 micron filters for aqueous solutions are also included. All materials must be stored in a fridge (2–8 degC).

These operations are preferably to be performed under sterile conditions. No more than 1 hour prior to dosing, one vial of prodrug is vented with a needle and hydrophobic filter. Sterile 2.15% w/v sodium hydrogen carbonate (10 ml) is then added directly through the bung via a syringe and needle. With the vent still in place the vial is swirled gently to obtain a clear solution (this will be 50 mg/ml as free base). The required dose volume is withdrawn into a sterile syringe through a sterile filter. The filter is then replaced by a sheathed sterile needle and the syringe unit kept cool prior to administration. Each remaining vial is prepared in an identical manner at intervals of one hour to allow for example three separate doses to be given 1 hour apart. Note this is used in combination with a suitable ADEPT antibody-enzyme conjugate such as antibody A5B7—carboxypeptidase G2 as described in international patent application WO 94/02450 and U.S. Pat. No. 5,405,990.

EXAMPLE 3

Anti-Tumour Activity

The anti-tumour activity of hydrogen iodide salt of N-(4-N,N-bis(2-iodoethyl)amino]phenoxycarbonyl)-L-glutamic acid (prodrug) has been demonstrated in the following model. LoVo tumour cells ($10^7$) (ECACC No: 87060101) are injected subcutaneously on the flank of athymic nude mice. When the tumour xenografts are 4–5 mm in diameter F(ab')$_2$A5B7-CPG2 conjugate (as described in international patent application WO 94/02450 and U.S. Pat. No. 5,405,990) is administered i.v. at a dose of 2.5 mg/kg (500U CPG2 activity/kg). Following a time interval (72 hr) to allow the conjugate to localise to the tumour and clear from blood and normal tissues, prodrug (3×70 mg/kg) is administered i.p. as 3 bolus doses, hourly, over a two hour period. This combination of conjugate and prodrug causes the tumour to regress and gives tumour growth delays of >30 days. Only minor effects on body weight and peripheral white blood cell counts are seen with this combination of conjugate and prodrug. Conjugate doses ranging from 0.25–10 mg/kg in combination with prodrug (3×50–90 mg/kg) have given significant anti-tumour activity in this model. Using 3 doses of prodrug over 2 hr gives better anti-tumour activity than a single dose.

Based on this anti-tumour data a clinical dose of conjugate would be in range 0.025–1.0 mg/kg, and more preferably 0.5–1.0 mg/kg. Prodrug would be administered once the conjugate had localised to the tumour and cleared from blood and normal tissues (conjugate level in plasma <1 μg/ml). Based on clinical data with the F(ab')$_2$A5B7-CPG2 conjugate (Bagshawe, Clinical Pharmacokinetic Concepts 27, 368, 1994) this is likely to be after 48–96 hr following conjugate administration. The dose of prodrug would be administered iv as 3 bolus doses, hourly, over a two hour period. Based on the mouse xenograft data anti-tumour activity in patients would be expected with a total dose of 15–150 mg/kg. However, standard dose escalation studies of prodrug would be used to define the optimal therapeutic dose.

EXAMPLE 4

X-Ray Powder Diffraction

Figure 3:
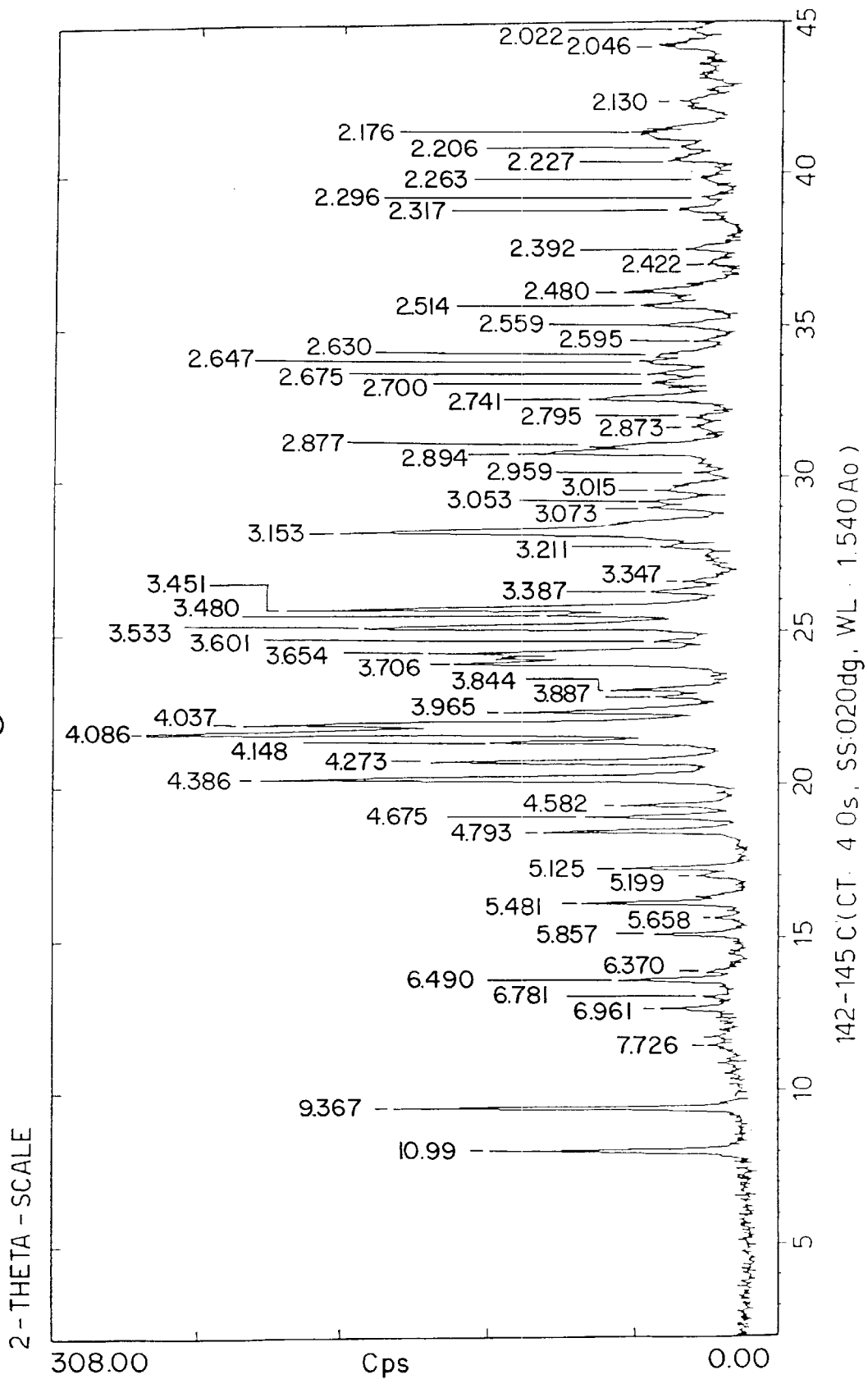
FIG. 3 shows a X-ray powder diffraction spectrum of the HI salt of the prodrug N-(4-[N,N-bis(2-iodoethyl)amino] phenoxycarbonyl)-L-glutamic acid in crystalline form.
Figure 4:
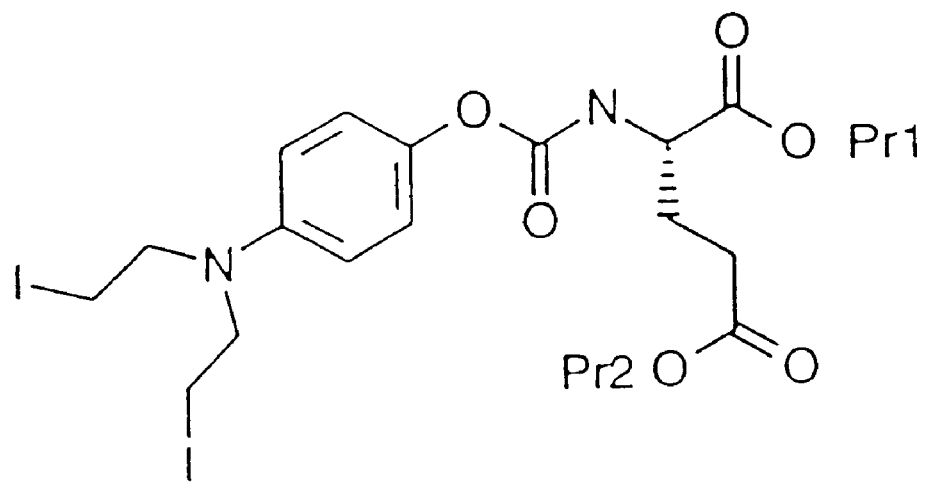
FIG. 4 shows a formula.

X-ray powder diffraction work was performed on a Siemens D5000™ Diffractometer. Approximately 1 gram of sample (hydrogen iodide salt of N-(4-[N,N-bis(2-iodoethyl)amino]phenoxycarbonyl)-L-glutamic acid in crystalline form) (sample should be in a finely ground physical form using a pestle and mortar, if necessary, whilst ensuring a minimum of work performed) was carefully front loaded into a standard Siemens mount and levelled with the aid of a standard glass microscope slide. The sample was spun at 30 rpm (this improves counting statistics) and irradiated with X-rays generated by: a 'copper long-fine focus tube' operated at 40 kV and 40 mA, wavelength of X-rays—1.5406 A (Angstroms). The collimated X-ray source was passed through an 'Automatic Variable Divergence Slit' set at V20 for constant area illumination over the entire Theta—Theta scan range and the reflected radiation passed through a 2 mm antiscatter slit and a 0.2 mm detector slit. Each sample was exposed for 4 seconds per 0.02 degrees 2-theta increment over the range 2 degrees to 45 degrees 2-theta (continuous scan). Each sample run, therefore, takes 2 hours 23 minutes and 20 seconds. The instrument is equipped with a Scintillation Counter as detector. Control and data capture is by means of a Dell 325P™ personal computer running with dedicated Diffrac AT™ (Socabim) software. FIG. 3 shows a diffraction spectrum of hydrogen iodide salt of N-(4[N-bis(2-iodoethyl)amino]phenoxycarbonyl)-L-glutamic acid in crystalline form.

We claim:

1. A hydrogen iodide salt of N-(4-[N,N-bis(2-iodoethyl)amino]phenoxycarbonyl)-L-glutamic acid.

2. A hydrogen iodide salt according to claim 1 in substantially pure form.

3. A hydrogen iodide salt according to any one of claims 1–2 in crystalline form.

4. A hydrogen iodide salt according to claim 3 in which the crystalline form has a melting point of 142–145° C.

5. A hydrogen iodide salt according to claim 3 in which the crystalline form has an X-ray powder diffraction spectrum substantially as shown in FIG. 3.

6. A pharmaceutical composition comprising a hydrogen iodide salt of N-(4-[N,N-bis(2-iodoethyl)amino]phenoxycarbonyl)-L-glutamic acid in substantially pure form and a pharmaceutically acceptable excipient.

7. A pharmaceutical composition according to claim 6 in dry form.

8. A pharmaceutical composition according to claim 7 in which the excipient is a buffer.

9. A pharmaceutical composition according to claim 8 in which the buffer is sodium bicarbonate.

10. A two component pharmaceutical composition comprising a first component which is a pharmaceutical composition as defined in any one of claims 6–9 and a second component which is a sterile diluent for reconstitution of the first component.

11. A process of making a hydrogen iodide salt of N-(4-[N,N-bis(2-iodoethyl)amino]phenoxycarbonyl)-L-glutamic acid in which the process comprises deprotecting a compound of Formula 1

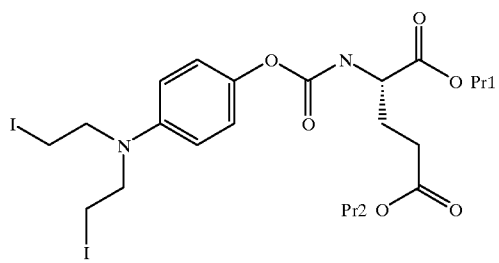

wherein Pr1 and Pr2 represent protecting groups in the presence of HI to produce a hydrogen iodide salt of N-(4-[N,N-bis(2-iodoethyl)amino]phenoxycarbonyl)-L-glutamic acid.

12. A process according to claim 11 in which Pr1 and Pr2 are tertiarybutyl ester groups.

13. A process according to claim 11 in which Pr1 and Pr2 are trimethylsilyl protecting groups.

14. A process of making a hydrogen iodide salt of N-(4-[N,N-bis(2-iodoethyl)amino]phenoxycarbonyl)-L-glutamic acid comprising deprotecting in 2 stages a compound of Formula 1

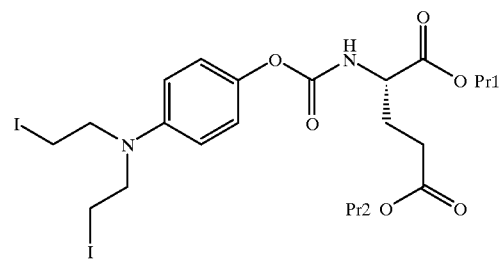

wherein $Pr^1$ and $Pr^2$ represent protecting groups, said process comprising:

$Pr^1$ and $Pr^2$ firstly being tertiarybutyl ester groups, and replacing said tertiarybutyl ester groups by second protecting groups which are trimethylsilyl groups; and removing the second protecting groups in the presence of HI to produce a hydrogen iodide salt of N-(4-[N,N-bis(2-iodoethyl)amino]phenoxycarbonyl)-L-glutamic acid.

15. A process of making a pharmaceutical composition comprising N-(4-[N,N-bis(2-iodoethyl)amino]phenoxycarbonyl)-L-glutamic acid in which the process comprises dissolving a hydrogen iodide salt of N-(4-[N,N-bis(2-iodoethyl)amino]phenoxycarbonyl)-L-glutamic acid in a buffer suitable for intravenous administration.

16. The process according to claim 15 in which the buffer is sodium bicarbonate.

* * * * *